United States Patent [19]

Moore

[11] Patent Number: 4,736,477
[45] Date of Patent: Apr. 12, 1988

[54] KNEE PILLOW
[75] Inventor: Gene M. Moore, St. Paul, Minn.
[73] Assignee: The Better Back Care Corporation, St. Paul, Minn.
[21] Appl. No.: 947,836
[22] Filed: Dec. 30, 1986
[51] Int. Cl.[4] .............................................. A47G 9/00
[52] U.S. Cl. ........................................ 5/443; 5/431; 128/88; 128/132 R; 128/165
[58] Field of Search ................ 5/443, 434, 436, 437, 5/444, 440, 465, 481, 431; 128/88, 132 R, 149, 165, 166; 2/22, 24

[56] References Cited
U.S. PATENT DOCUMENTS

| | | | |
|---|---|---|---|
| 3,757,365 | 9/1973 | Kretchmer | 5/436 |
| 4,019,504 | 4/1977 | Sterling | 128/88 |
| 4,177,806 | 12/1979 | Griffin | 5/443 |
| 4,210,317 | 7/1980 | Spann et al. | 5/431 |
| 4,392,489 | 7/1983 | Wagner, Sr. | 5/443 |

FOREIGN PATENT DOCUMENTS

| | | | |
|---|---|---|---|
| 6602793 | 9/1966 | Netherlands | 5/465 |
| 2085708 | 5/1982 | United Kingdom | 2/24 |

Primary Examiner—Alexander Grosz
Attorney, Agent, or Firm—Merchant, Gould, Smith, Edell, Welter & Schmidt

[57] ABSTRACT

A pillow (1) which may be placed between the knees (22, 26) of a leg (20), so as to prevent chafing between the knees when a person is required to recline on their side for a long period of time. The pillow (1) is generally rectangular in plan form, and includes a series of notches (6, 7, 8) which permit the pillow to deflect in a manner consistent with the movement of the knee. A plurality of straps (14, 17) are used to fasten the pillow to the knee, fastening of the straps being accomplished by means of hookable fasteners (15, 18).

2 Claims, 2 Drawing Sheets

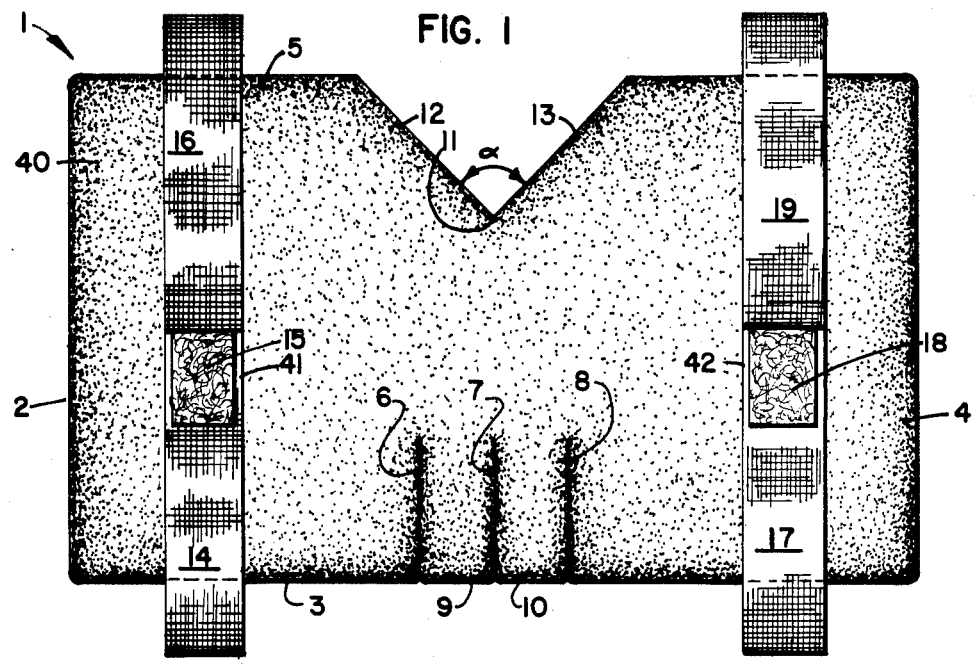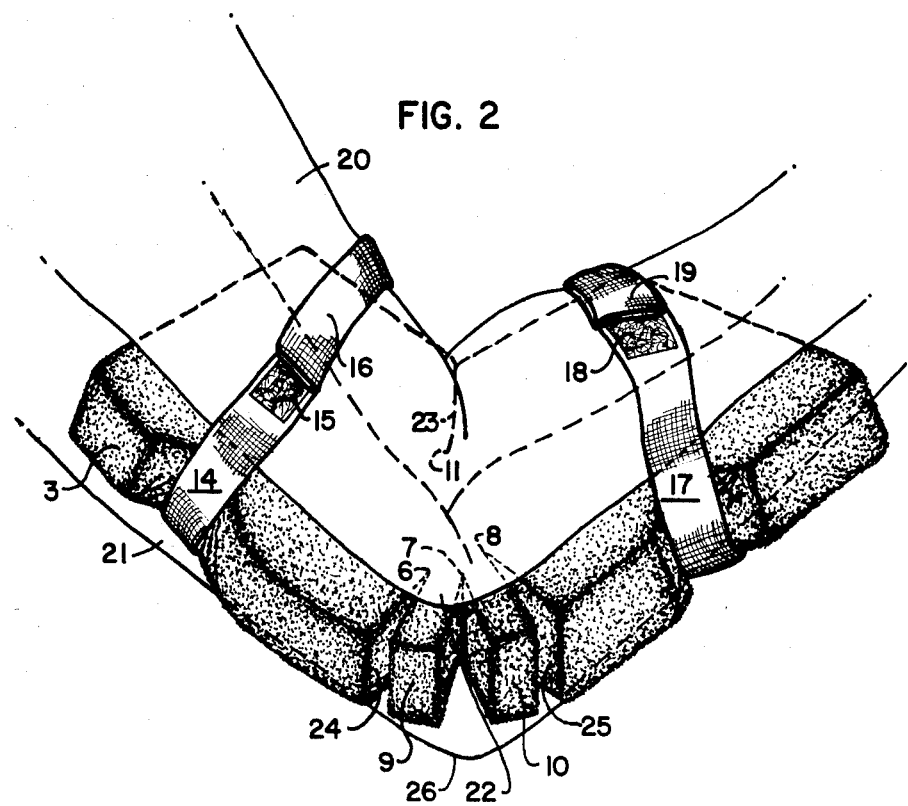

KNEE PILLOW

FIELD OF THE INVENTION

The field of the invention is that of health aids and more particularly apparatus used to assist in sleeping and reclining comfortably. The particular improvement of the invention is a pillow adapted to prevent chafing between portions of adjacent limbs.

BACKGROUND OF THE INVENTION

The present invention relates to a knee pillow, and more particularly to a knee pillow which can be positioned between the patient's legs to facilitate restful sleep.

Many people have medical problems which interfere with their sleep. These problems include back discomfort caused by nerve irritation or trauma, painful arthritis, knee conditions, and sacroiliac discomfort. Similarly, persons who suffer from paralysis of their lower extremities must necessarily remain in positions, either sitting or reclining, in which the relative position of their knees and ankles change little, although slight motion occurs on a regular basis, such as when the patient is lifted or turned by others. Prolonged contact of the knees and ankles can lead to bruising or chafing. Finally, persons recovering from certain medical procedures, or pregnant women, are often required to rest or sleep in positions that result in prolonged contact of the knees and ankles, thereby necessitating some mechanism for comfortably preventing such contact.

To facilitate a restful sleep, doctors have long recommended that patients having these and other problems sleep on their side with a pillow placed between their legs. However, there are several problems associated with the placement of a conventional pillow between the patient's legs. A conventional pillow is not shaped properly, and it is difficult to position a conventional pillow comfortably between the patient's legs. Further, the conventional pillow is easily displaced during the night due to the patient's movement, necessitating an inconvenient and often difficult repositioning of the pillow.

SUMMARY OF THE INVENTION

The knee pillow of the present invention comprises a flexible pillow member having a plurality of straps which go around the patient's leg. In the first embodiment of the present invention, the knee pillow is disposed proximate the patient's knee, and the straps are positioned around the patient's lower thigh and upper calf. In the second embodiment of the present invention, the knee pillow extends from above the knee down to the patient's ankle and includes a stirrup-type strap extending around the patient's foot.

A particular advantage of the present invention is that the knee pillow provides for a more comfortable, restful sleep for patients suffering from various leg and back conditions. The knee pillow also protects the tender, injured areas of the body, and reduces the likelihood of problems relating to meniscus and ligaments. Another advantage of the present invention is that the patient is able to move in bed without the necessity of repositioning the knee pillow. The patient can also easily and comfortably get up from bed and walk around without repositioning the knee pillow.

Another feature of the present invention is that the straps which go around the patient's leg are comfortable and easy to attach. The flexible straps do not cut off circulation, and the Velcro TM fasteners are easily adjustable and provide for a secure attachment.

These and various other advantages and features of novelty which characterize the invention are pointed out with particularity in the claims annexed hereto and forming a part hereof. However, for a better understanding of the invention, its advantages, and objectives obtained by its use, reference should be had to the drawings which form a further part hereof and to the accompanying descriptive matter, in which there is illustrated and described the preferred embodiment of the invention.

BRIEF DESCRIPTION OF THE DRAWINGS

FIG. 1 is a plan view of a first preferred embodiment of a knee pillow constructed in accordance with the principles of the present invention.

FIG. 2 is a perspective view of the knee pillow as shown in FIG. 1, depicted in use in conjunction with a human knee.

DESCRIPTION OF THE PREFERRED EMBODIMENT

Figure 3:
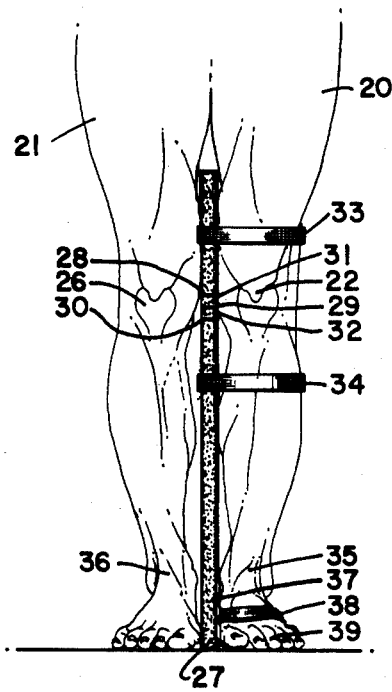
FIG. 3 is a pictorial view of a second embodiment of a knee pillow.

As best seen in FIG. 1, a knee pillow constructed according to the principles of the present invention is shown generally at 1. The pillow comprises a generally rectangular planform including a left side 2, a leading side 3, a right side 4, and a trailing side 5. In the preferred embodiment, sides 2 and 4 would be of approximately the same length, the length being within the range of 6 to 10 inches. The leading side 3 would have a somewhat longer dimension than the left and right sides, on the order of 12 to 15 inches. As can best be seen in FIG. 2, the pillow 1 is of approximately uniform thickness, with leading side 3, for example, being approximately 1 to 2 inches thick.

One novel aspect of the present invention resides in the method provided to permit flexure of the pillow under a variety of conditions. As seen in FIGS. 1 and 2, the leading side 3 contains a series of notches, such as, for example, in the embodiment shown, a first notch 6, a second notch 7 and a third notch 8. The notches 6 and 7 result in the formation of a first flexible segment 9, while the notches 7 and 8 create a second flexible segment 10.

As shown in FIG. 1, the trailing side 5 includes a groove 11, the groove forming left wall 12 and right wall 13. Typically, the angle $\alpha$ formed between left wall 12 and right wall 13 is in the range of 100 degrees to 40 degrees. The angle $\alpha$ formed between left wall 12 and right wall 13 is at a maximum value when the pillow 1 is in a normal, unused, undeflected position as depicted in FIG. 1.

Permanently attached to the pillow 1 is a left strap 14, which is typically achieved by sewing the strap directly to the outer surface of the pillow 1. Ideally, the strap 14 has a strip of a hookable mat material 15 (such as Velcro TM ) affixed to its outer surface 41 in a region overlying the surface 40 of pillow 1. The inner surface of the strap 14 (not shown) may then be covered with a hookable fastener (not shown) which may be securely attached to mat 15, thereby permitting the strap to be secured in place by simply contacting end portion 16 of strap 14 with the mat 15. A substantially identical strap 17 is affixed to the region of pillow 1 opposite groove 11, strap 17 having a mat type fastener 18 suitably attached to its outer surface 42 overlying the surface 40 of pillow 1 so as to mate with hookable fasteners (not shown) attached to the under side of end 19.

As best seen in FIG. 2, the pillow may be most advantageously used by placing it between the left leg 20 and the right leg 21 of a person resting on their side. The pillow may be secured in place by, for example, placing strap 14 around leg 20 above the knee 22 and placing strap 17 around leg 20 below the region of knee 22. The straps may be secured in place by fastening their respective ends 16 and 19 to their mating attachment mats 15 and 18. As shown in FIG. 2, when the knee 22 is bent, the left wall 12 and right wall 13 of groove 11 will be deflected toward each other, to the extent that walls 12 and 13 meet and form a single line of contact 23. Simultaneously, flexible segments 9 and 10 separate both from each other and the adjoining side walls 24 and 25 of leading side 3, thereby permitting a substantial portion of the pillow 1 to remain aligned with those portions of the leg both above and below the knee 22. Note that flexible segments 9 and 10 still reside within the region of knee 22 and prevent its contact with adjoining right knee 26. In this fashion, the entire portion of the legs 20 and 21, both above and below knees 22 and 26 are in contact with the pillow 1 regardless of the degree of deflection of the knee 22.

An alternate preferred embodiment is shown in FIG. 3. In this embodiment, a pillow 27 is shown placed between left leg 20 and right leg 21. Grooves 28, 29 and 30 define flexible segments 31 and 32, thereby allowing deflection of pillow 27 when the knee 22 is bent, in a manner similar to that depicted in FIGS. 1 and 2. A thigh strap 33 is used to secure the pillow to leg 20 in the region above knee 22, whereas shin strap 34 is used to secure pillow 27 to leg 20 in the region below knee 22.

Pillow 27 is suitably dimensioned so that it extends from a region above the knee 22 to an area below ankle 35, thereby preventing chafing between both the adjacent knees 22 and 26 and adjacent ankles 35 and 36. The lower portion 37 of pillow 27 is secured in place by means of an elastic stirrup 38 which may be secured in place by inserting foot 39 through stirrup 38.

The construction of both pillows 1 and 27 may be accomplished by covering a medium density foam core with a suitable plastic or cloth covering. The only requirements for the foam core are that it be resilient and deformable, while the covering must be resistant to tearing, staining and the corrosive effects of human perspiration.

The foregoing disclosure is a representative form of the invention and is to be interpreted in an illustrative rather than a limiting sense, the invention to be accorded the full scope of the claims appended hereto.

I claim:

1. A pillow adapted to be used between two human legs, in the knee region, comprising:
    (a) a core, the core being formed of a relatively deformable, resilient material, wherein the core is generally formed in the shape of a rectangular solid, the rectangular solid having a height, width, a length, a longitudinal axis, and residing within a plane, the core being formed from a material having substantially the characteristics of a medium density foam;
    (b) a covering, the covering being compatibly shaped so as to fully encompass the core;
    (c) means for affixing the pillow to a human leg;
    (d) a leading side, wherein the leading side of the pillow is segmented by a plurality of notches, the notches forming a plurality of segments such that the pillow may be deflected while remaining within the plane defined by the rectangular core;
    (e) a left side, the left side orthogonally adjoining the leading side;
    (f) a right side, the right side orthogonally adjoining the leading side, the right side being oppositely disposed in parallel to the left side;
    (g) a trailing side, the trailing side being oppositely disposed from the leading side, the trailing side orthogonally adjoining the left side and the right side, the trailing side containing a groove, the groove having a central notched portion, a right side, and a left side, the right side and the left side forming an angle which is at a maximum value when the pillow is undeflected; and
    (h) a plurality of straps, each strap being substantially identical, each strap being permanently affixed to the pillow, each strap being aligned so as to be substantially parallel to the left and right sides of the pillow, the straps serving as a means for affixing the pillow to a human leg, the strap further comprising:
        (i) a first side, the first side having a loose end, the loose end being covered with a hookable fastener, the first side having a fixed end, the fixed end being permanently affixed to the pillow; and
        (ii) a second side, the second side having a hookable mat fastener attached adjacent to the fixed end of the first side, the hookable fastener being adapted so as to grip the hookable fastener of the first side;
    the pillow further comprising a stirrup, formed of an elastic material, shaped so as to accept the insertion of a human foot, said stirrup being permanently affixed to a side of the pillow.

2. The pillow of claim 1, wherein the angle formed between the right side and the left side of the groove is between 100 degrees and 40 degrees when the pillow is undeflected, the angle being capable of reducing to zero when the pillow is deflected.

* * * * *